(12) United States Patent
Stidham et al.

(10) Patent No.: US 6,355,278 B1
(45) Date of Patent: Mar. 12, 2002

(54) DRY DAIRY COW SUPPLEMENT

(75) Inventors: William D. Stidham, Glidden; Donald W. Seaman, Ralston; Myron F. Danzer; James P. Henry, both of Glidden, all of IA (US)

(73) Assignee: West Central Cooperative, Ralston, IA (US)

( * ) Notice: Subject to any disclaimer, the term of this patent is extended or adjusted under 35 U.S.C. 154(b) by 0 days.

(21) Appl. No.: 09/282,876

(22) Filed: Mar. 31, 1999

(51) Int. Cl.[7] .................. A61K 33/20; A61K 33/06; A61K 35/78; A61K 47/00; A23K 1/00
(52) U.S. Cl. .................. 424/666; 424/439; 424/442; 424/683; 424/687; 424/692; 424/725; 424/750; 424/757; 424/773; 424/776; 426/623; 426/630; 426/635; 426/807; 514/769; 514/770; 514/783; 514/974
(58) Field of Search ................. 424/666, 439, 424/442, 683, 687, 692, 725, 750, 757, 773, 776; 426/623, 624, 630, 635, 807; 514/769, 770, 783, 974

(56) References Cited

U.S. PATENT DOCUMENTS

| | | | |
|---|---|---|---|
| 4,391,839 A | * 7/1983 | Devenyi et al. | 426/626 |
| 4,931,290 A | 6/1990 | Rebhan | |
| 5,225,230 A | * 7/1993 | Seaman et al. | 426/634 |
| 5,260,089 A | * 11/1993 | Thornberg | 426/624 |
| 5,393,535 A | 2/1995 | Kjems | |
| 5,560,920 A | 10/1996 | Goff et al. | |
| 5,631,289 A | 5/1997 | Abele | |
| 5,935,635 A | * 8/1999 | Mori et al. | 426/656 |
| 5,997,939 A | * 12/1999 | Moechnig et al. | 426/656 |

OTHER PUBLICATIONS

Goff et al., 'Assessment of hydrochloric acid as a source of anions for adjusting dietary cation–anion difference' (1996), Journal of Diary Science, vol. 79, Supp. 1, p. 198.*
Hoard's Dairyman; Fresh Cow Problems are Costly; Culling Hurst the Most (Jan. 1996).
R. L. Horst, J. P. Goff, T. A. Reinhardt and D. R. Buxton; Strategies for Preventing Milk Fever in Dairy Cattle; Journal Dairy Science; vol. 80; No. 7 (1997) pp. 1269–1280.
M. E. Ensminger, B.S., M.S., Ph.D.; Dairy Cattle Science; pp. 9 and pp. 287 (1993).
J.P. Goff and R.L. Horst; Use of Hydrochloric Acid as a Source of Anions for Prevention of Milk Fever; Journal Dairy Science; vol. 81; No. 11 (1998) pp. 2874–2880.

* cited by examiner

*Primary Examiner*—Jose' G. Dees
*Assistant Examiner*—Frank Choi
(74) *Attorney, Agent, or Firm*—Fay, Sharpe, Fagan, Minnich & McKee, LLP

(57) ABSTRACT

A formulation for preventing or treating parturient hypocalcemia or milk fever comprises a solution of hydrochloric acid in water, soybean meal, additional feed components and minerals. The feed formulation is prepared by grinding soybean meal to a particle size of 1000 to 2000 microns. A hydrochloric acid solution and feedgrade limestone are blended into the meal to produce the formulation.

9 Claims, 2 Drawing Sheets

DRY DAIRY COW SUPPLEMENT

BACKGROUND OF THE INVENTION

This invention relates to a range of products and the art of preparing those products for inhibiting the effects of or reducing the risk of contracting a disease which, in many cases, has a significant impact on the economics of dairy farming.

The disease is parturient hypocalcemia or milk fever. This is a condition, to quote Ensminger, ("Dairy Cattle Science," M. E. Ensminger, Third edition (1993), Interstate Publishers, p. 287): "At or soon after calving (generally within 48 to 72 hours), a sharp decrease in blood calcium (hypocalcemia) occurs in some cows, resulting in a loss of appetite, subnormal temperature, and an unsteady gait. This is followed by nervousness, and, finally, collapse or complete loss of consciousness." The triggering mechanism for the hypocalcemia, i.e., drop in blood calcium is the onset of lactation which causes an intensive mobilization of calcium. Unless treated, the disease can cause death and, therefore, the loss of the animal as a future milk producer.

The losses to the dairy farm economic sector can be significant. The total number of milk cows in the United States is in the order of 10 million. (See, for example, Ensminger, op. cit., p. 9), of which perhaps 60% are pari-parturient and at risk for the disease. From a total milk production point of view alone, the 10 million milk cows represent about 1,500 billion pounds of milk in a given year. It is estimated that approximately 8% of all lactating cows are affected by clinical milk fever. It has also been estimated (Horst, et al., 1997) that the disease can reduce the productive life of a dairy cow by 3.5 years. Based upon its studies (C. Guard, Cornell Veterinary College, as reported in Hoard's Dairyman, January 1996) Cornell University further estimated that the average cost per milk fever case was $334. This value represented the direct cost of treating the clinical cases and the estimated production losses of milk. Multiplying the number of potential cases by the $334 per case yields an estimated total loss to the U.S. dairy industry of $160 million per year. Another factor affecting economic losses is that milk cows contracting milk fever are also more susceptible to a host of secondary problems, which include ketosis, mastitis, dystocia, retained placenta, displaced abomassum and uterine prolapse (Horst et al., 1997). Each of these secondary problems has as the least consequence a reduction or further reduction of milk production.

Since milk fever has such a major impact on the economy of dairy farming in the United States and elsewhere in the world, a considerable amount of research has been directed towards its prevention and cure.

Perhaps the most significant early research was reported by a group of Norwegian researchers (Ender, F. and I. W. Dishington, 1967, "Comparative Studies on Calcium Balance Levels in Parturient Cows Fed Diets Inducing and Preventing Milk Fever." 557Am XVIIIth World Veterinary, Congress, Paris, France) who demonstrated that the effect of various cations in dietary rations of a dairy cow in terms of promoting milk fever incidence could be prevented by adding anions in the form of hydrochloric and sulfuric acid. However, they realized that with the other feed ingredients at their disposal at the time, using these highly corrosive acids in their un-reacted forms would pose a serious hazard to both dairy cattle and dairy farm personnel. Thus, the conclusion of these researchers was that instead of these pure acids, related anionic salts, such as calcium chloride, ammonium sulfate, aluminum sulfate and magnesium sulfate, should be considered.

Based upon these findings, other researchers (most prominently Goff and Horst) then started evaluating these anionic salts. They found that while these salts are relatively easy to handle, there are a) problems of palatability and b) the intrinsic problem that while salts contain anions, they also contain cations which, depending upon their rate of absorption, will negate some of the positive effects of the anions.

The same paper (J. R. Goff and R. L. Horst, "Using Hydrochloric Acid as a Source of Anions for Prevention of Milk Fever", USDA Prepublication (1997)) compares hydrochloric acid with the anionic salt calcium chloride and shows the advantage of the former over the latter. The authors also discuss in some detail comparative feeding studies involving dairy cow diets with or without hydrochloric acid and show the ability of a diet with hydrochloric acid to control milk fever. In a subsequent paper, "Use of Hydrochloric Acid as a Source of Anions for Prevention of Milk Fever", J. Dairy Science, November 1998, p. 2874–2880), the same authors, Goff and Horst, provide further evidence for their earlier conclusions.

While this paper is substantive in its proof that, to quote the authors, "hydrochloric acid is an inexpensive, 'palatable' alternative to anionic salts as a means of controlling milk fever," the palatability is only improved as compared to those of the anionic salts. Hydrochloric acid used with the formulations studied is still difficult to administer as the dairy cow does not want to consume it in the quantities required.

Because of the problems mentioned, with respect to acids, past research was focused on preparing formulations using anionic salts and not those using hydrochloric or sulfuric acids.

For example, Rebhan (Herbert J. Rebhan, U.S. Pat. No. 4,931,290, "Milk Fever Prophylactic Treatment and Composition) describes a method for "reducing the propensity of a dairy cow to develop severe milk fever upon calving comprising of administering thereto a composition (consisting) of a water soluble calcium compound and a complexing agent for serum phosphorus." That patent discusses the use of (anionic) calcium salts of hydrochloric and organic acids supplemented with a complexing agent to form water-insoluble compounds of serum phosphorus. The combinations of these compounds are presented as having a favorable effect on the blood anion-cation balance and, thereby reducing the incidence or curing milk fever.

A further example, Kjems (Gunnar Kjems, U.S. Pat. No. 5,393,535, "Orally Administrable Calcium Supplement for Cattle"), describes a composition wherein a calcium ion, i.e., an anionic salt is dissolved in water but the water phase is dispersed into a continuous oil phase, forming an emulsion by means of a nonionic emulsifier. This method of preparation is presented as compatible with oral administration of the composition and as palatable to the dairy cow because of the oily phase.

In another example, Goff and Horst (Jesse P. Goff and Ronald L. Horst, U.S. Pat. No. 5,560,920, "Calcium Formulations for Prevention of Parturient Hypocalcemia") present that calcium propionate, i.e., an anionic organic salt may be mixed with propylene glycol and either citric or phosphoric acid to form a nonhardening paste or with sodium chloride to form a liquid drench. It is stated that these formulations are particularly effective in treating the hypocalcemia associated with the onset of lactation in dairy cows. The inventors argue that calcium-containing gels can be made with water-insoluble carriers (as discussed by Kjems) such as oils or with water-soluble carriers such as propylene glycol. They state that the former tends to decrease the availability of calcium for absorption, but that the gels formed with propylene glycol are more readily soluble in water and thereby increase the availability of calcium.

In still another example, Abele (Ulf Abele, U.S. Pat. No. 5,631,289, "Use of Calcium Formate in Orally Administrable Compositions"), discusses the advantages of an anionic salt of formic acid, i.e., calcium formate in the prophylaxis and metaphylaxis of calcium deficiency in dairy cows. It is stated that the resorption of calcium formate is comparable to that of calcium chloride, but that the former is not corrosive or irritating to the membranes of the digestive tract and thus it is both more palatable and is also less dangerous to the animal if per chance the formulation is inhaled in the respiratory tract, as compared to calcium chloride formulations. Even so, the patent recommends that the calcium formate be bound in a gel or paste to further improve palatability and further lessen the chance of ingestion into the respiratory tract.

The background material presented above summarizes current knowledge. That knowledge may also be stated as follows:

To reduce the incidence of or cure milk fever, it is important that the dry cow has the proper anion-cation balance in its body fluids. There is an equation, referred to as the "dietary cation-anion difference equation," which describes the effect diet cations and anions will have on blood and urine pH of the dry cow. This equation shows dietary effects of the individual ions, such as the cation sodium, potassium, calcium and magnesium and the anions, chlorine, sulfur and phosphorus. Based upon other dietary considerations, phosphorus, magnesium and sulfur (in its sulfate form) and calcium have certain intake limitations. Sodium and potassium should be kept as low as possible in keeping with the management of the forages available. Dietary chlorine should be optimally kept at 0.8 percent by weight. Monitoring urine pH is the best means to determine if more or less anions are needed. A typical target is a pH of 6.2 to 6.7 in Holstein cows.

The products of the present invention are highly palatable and, therefore readily consumed by the dry cow. They are highly effective in controlling urine pH and maintaining it within the desirable range and thus inhibiting the effects or reducing the risk of contracting the disease.

BRIEF SUMMARY OF THE INVENTION

The invention presented here relates to a range of products for inhibiting the effects or reducing the risk of contracting parturient hypocalcemia or milk fever in dairy cows and to a method for preparing same. These products are prepared using a soybean meal extracted from soybeans which were treated according to a method described in detail in U.S. Pat. No. 5,225,230, incorporated herein by reference.

In accordance with the present invention, soybean meal prepared according the method of U.S. Pat. No. 5,224,230 is mixed with hydrochloric acid and other ingredients to enhance or balance the feed value of the mix to form a product that in relatively small daily dosages prevents and treats milk fever in dairy cows as it is readily consumed by the animal because of its high degree of palatability.

Soybeans are comminuted to a particle size range suitable for the physical and chemical reactions of the subsequent steps.

Next, the comminuted soybean particles are reacted at a high temperature, in the range of about 235 to 350 degrees Fahrenheit, for the purpose of converting the soybean solids contained therein into a high bypass protein product. The high temperature heated soybean particles are subsequently fed to a screw press for the mechanical removal of soybean oil. The solid product discharging from the press is generally referred to as soybean press cake. This product is subsequently ground to produce a high bypass protein meal.

To prepare a formulation, the high bypass protein meal prepared from soybeans is mixed in a blender vessel with a quantity of hydrochloric acid of an appropriate Baume strength for a period of time to allow the hydrochloric acid to be completely absorbed and homogeneously blended.

One significant formulation consists of one part by weight of Baumé (36% acid by weight) hydrochloric acid added to three parts by weight of the high bypass soybean meal. This formulation could contain up to 25% moisture by weight. Further increasing the concentration of hydrochloric acid, i.e., increasing the Baumé strength over 22, results in a product with excessive hydrochloric acid odor.

Another significant formulation consists of one part by weight of 20 Baumé (31.5% by weight) hydrochloric acid added to 3 parts by weight of high bypass soybean meal. Formulating this product with a much lower Baumé, i.e., a lower concentration would result in a product that is too wet and therefore may cause materials handling problems. The lowest Baumé is considered 18 (approximately 27.5% by weight). One part of this acid added to 3 parts of high bypass soybean meal would contain up to 28.6% of moisture by weight.

To prepare a range of additional formulations, a quantity of the high bypass protein meal prepared from soybean is mixed in a blender vessel with a quantity of hydrochloric acid of an appropriate Baume strength and one or more further ingredients for the purpose of further increasing palatability, controlling the strong hydrochloric acid odor, dust control and prevention of particulate matter entering the animal's respiratory tract and improving the nutritive balance of the mix in terms of energy, nitrogen, fiber and mineral content.

One ingredient found useful in controlling hydrochloric acid odor is calcium carbonate, which best should be used in its commercially available form such as feed grade limestone or ground oyster shells. One part of either feed grade limestone or ground oyster shells may be added to each four to six parts of hydrochloric acid in the mix.

A benefit of the present invention is that the high temperature step in preparing the soybean material for subsequent mechanical removal of oil, i.e., screw pressing, results in solids which, once ground to form a meal, are highly palatable in their own right and show enhanced palatability once blended with hydrochloric acid.

Yet another benefit of the present invention is that the milk fever inhibiting properties of the specially high temperature treated soybean meal with hydrochloric acid can be further enhanced by blending in ingredients which add further desirable medical and nutritive properties.

Still other benefits and advantages of the present invention will become apparent to those skilled in the art upon reading and understanding of the following detailed description.

BRIEF DESCRIPTION OF THE DRAWINGS

The invention may take physical form in certain parts and arrangements of parts, a preferred embodiment of which will be described in detail in this specification and illustrated in the accompanying drawings which form a part hereof.

DETAILED DESCRIPTION OF THE INVENTION

Figure 1:
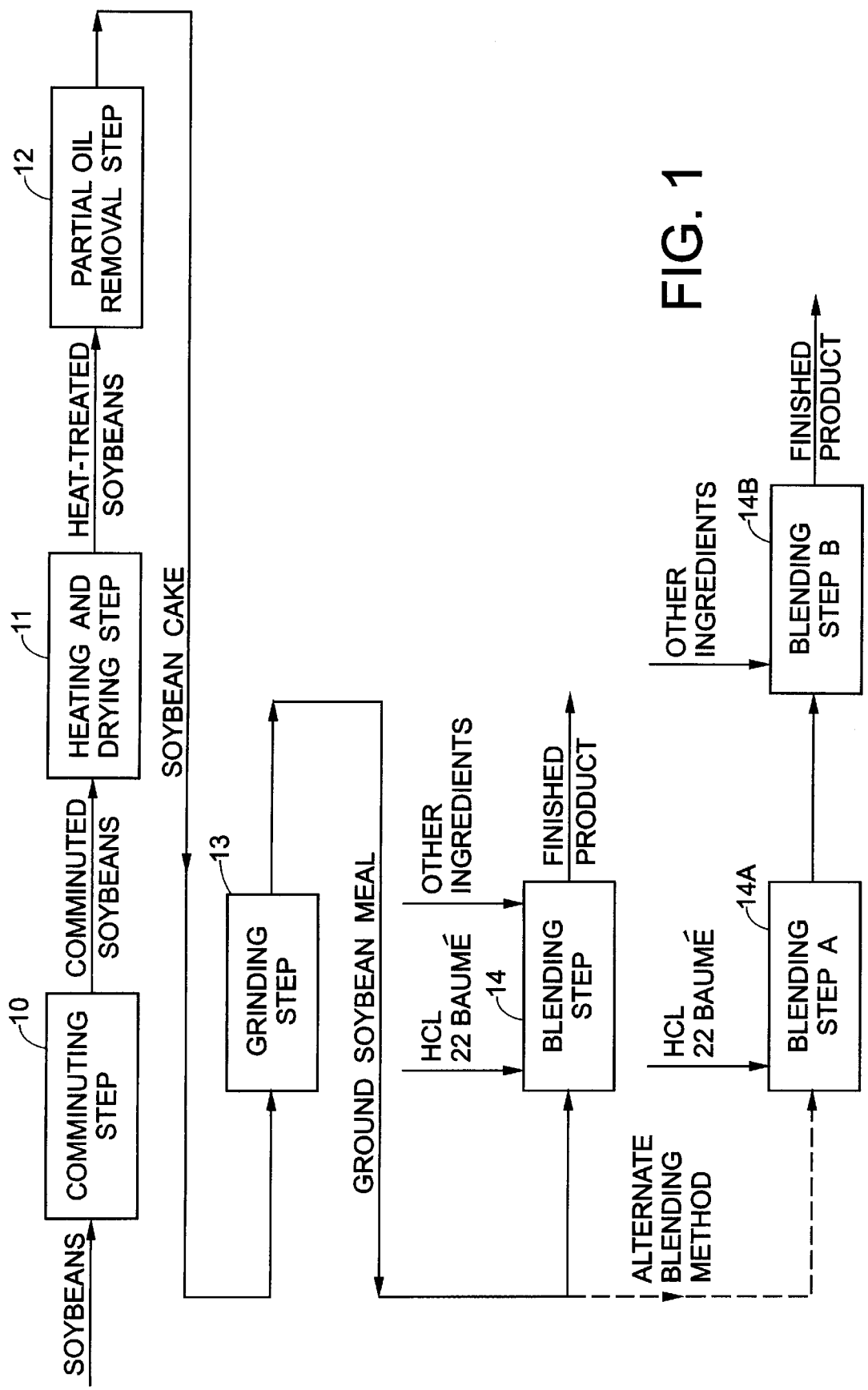
FIG. 1 is a block diagram illustrating the steps in the practice of the present invention for producing formulations consisting of a specially treated soybean meal, hydrochloric acid and other ingredients.

Referring now to the drawings wherein the showings are for purposes of illustrating the preferred embodiments of the invention only and not for the purposes of limiting same, FIG. 1 is a block diagram showing the steps followed in practicing the present invention. In particular, FIG. 1 sets forth the steps of comminuting the soybeans, heating and full pressing the soybean material to substantially remove the soybean oil therefrom, grinding the compacted soybean material discharging from the full pressing equipment, i.e., the full press cake, to produce a high-temperature treated soybean meal, blending that meal with hydrochloric acid of a desired Baume strength and other ingredients. A description of the relevant steps of the subject invention would include the comminuting step (block 10), the heating and drying step (block 11), the partial oil removal step (block 12), the grinding step (block 13) and the blending step or steps (block 14 or a sequence of blocks 14A, 14B, or more).

Block 10 shows the comminuting step in which soybeans from a storage source are comminuted to a desired particle size range. A practical range is from smaller than 200 mesh to as large as approximately one-eight of an inch in average diameter.

Block 11 in FIG. 1 represents a high-temperature heating, step. At this point the comminuted soybeans are heated at elevated temperatures in the range of about 235 to 350 degrees Fahrenheit and maintained at these elevated temperatures for about 1 to 60 minutes. Since the process of heating the soybeans causes the soybeans to lose moisture, i.e., to dry, this step is referred to as a "heating and drying" step. The objective of this step, relevant to the present invention, is to convert the soybean solids into a product which not only has desirable nutritive properties, as elaborated in U.S. Pat. No. 5,225,230, but also is a superior admixture with hydrochloric acid, the known anionic compound to inhibit the effects or reduce the risk of contracting milk fever and with other desirable ingredients.

Block 12 on FIG. 1 represents the partial removal of the soybean oil from the soybeans by mechanical means. This step is important for several reasons: a) the soybean oil has an economic value of its own as a precursor for food and industrial products and b) retaining the oil would yield a product with too much oil for a good dairy feed ration or supplement.

Block 13 on FIG. 1 shows the grinding step in which the compacted discharge (usually referred to as soybean press cake) from the previous step is ground to a particle size (typically 1,000 to 1,200 microns), i.e., a particle size range with particles small enough for easy admixture with and complete absorption of hydrochloric acid but not too small to cause dust problems with its associated losses and possible ingestion in the respiratory tract.

Block 14 on FIG. 1 shows the blending step in which the ground soybean press cake is introduced into a stirred vessel together with the hydrochloric acid ingredient and with other ingredients as desired.

Blocks 14A and 14B show an alternate blending step in which the ingredients are admixed sequentially, i.e. one or more ingredients are added after two or more of the other ingredients have been blended.

Figure 2:
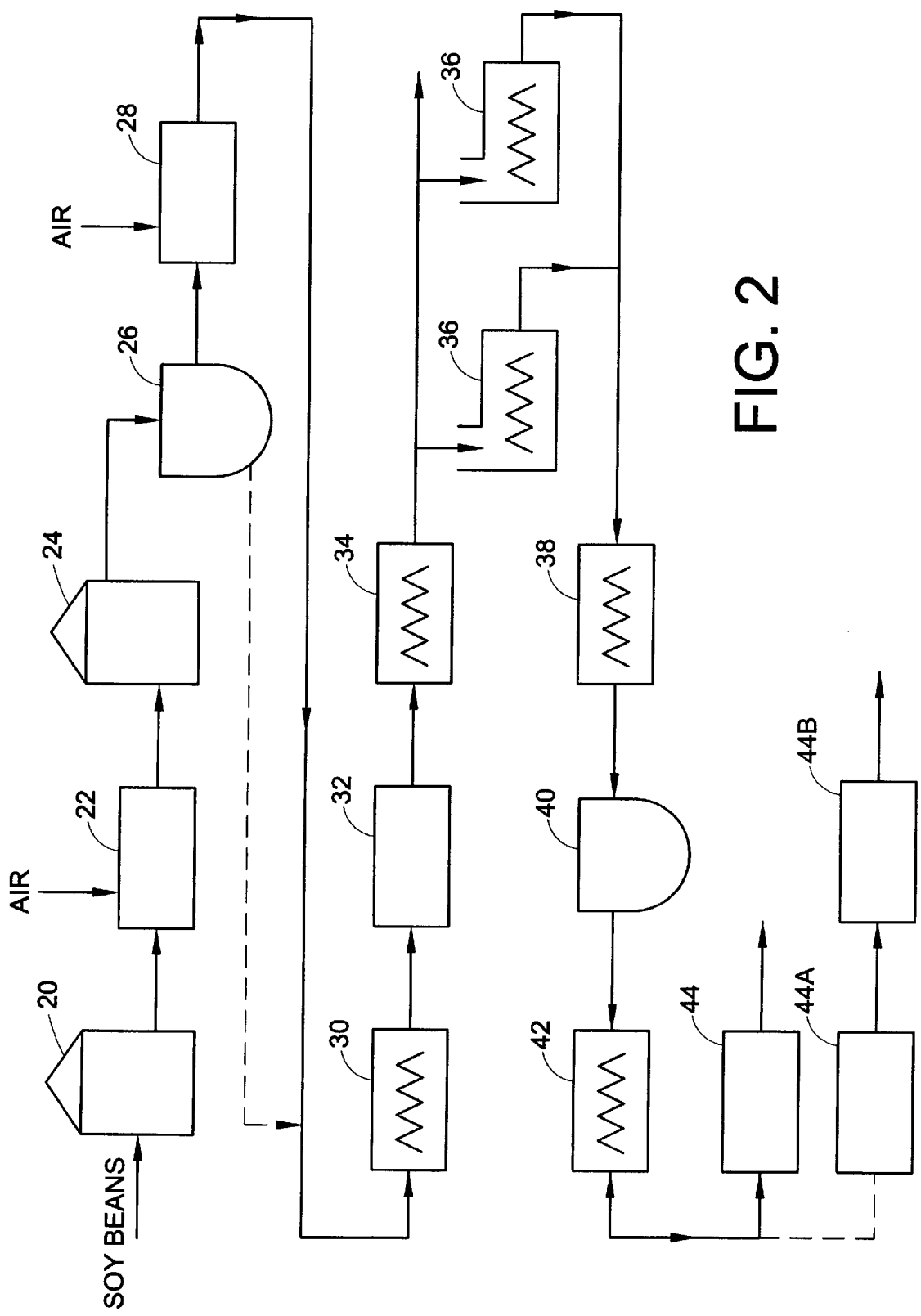
FIG. 2 is a schematic diagram of a plant constructed with the present invention for producing the specially treated soybean meal and admixing this meal with hydrochloric acid and other ingredients.

Turning now to FIG. 2, a schematic representation of a plant constructed in accordance with the present invention is shown. Reference is made to U.S. Pat. No. 5,225,230, incorporated herein by reference, for further technical details prior to grinding the soybean press cake.

Harvested soybeans are delivered to the processing plant and directed to a receiving or holding tank 20 from where they are discharged to conveyors that conduct the soybeans to the cleaning equipment 22. The purpose of the cleaning step is to remove dirt, twigs, and other items.

After they have been cleaned, the soybeans may be stored in a storage bin 24 and held for processing at a later date. Alternatively, the cleaned soybeans may be transmitted directly from storage bin 24 for further processing.

Next, the soybeans are transferred to comminuting equipment 26. Here, the soybeans are comminuted using equipment commonly used for these purposes and known to those skilled in the art of soybean processing. Examples of such comminuting equipment are cracking rolls and hammer mills.

An optional step may comprise dehulling of the soybeans to remove a smaller or larger portion of the hulls. If it is desired to dehull or partially dehull the soybeans, the comminuted soybeans are transferred to hull removal equipment 28 which causes air to flow through the cracked beans and hulls, for the purpose of dislodging and carrying away the hulls. As such, removal of the hulls may positively affect the quality parameters of the meals and it may also prevent excessive wear of the equipment for soybean oil removal, but it does not affect the subsequent processing steps leading up to preparation of product which is an admixture of the soybean solids and hydrochloric acid or the soybean solids, hydrochloric acid and other ingredients.

The comminuted soybeans are conducted by means of conveyor 30 to the high temperature reactor 32. The physical form of the reactor is conducive to heating and maintaining the soybean particles at a temperature range of roughly 235 to 350 degrees Fahrenheit for a period of between about 1–60 minutes in order to condition the soybean solids in the soybean particles to increase ;bypass protein content, improve palatability and condition the solids for the subsequent admixture of hydrochloric acid. The conditioned soybean particles are conducted to the subsequent step by means of a conveyor or conveyor system 34.

A further step is to mechanically extract the comminuted and heated and conditioned soybean particles in a screw press or bank of screw presses 36 which is also used in conventional soybean processing for this same purpose. The objective of this step is to substantially remove the soybean oil which is further processed to prepare products unrelated to this invention. The soybean solids which are highly compacted upon discharge from the screw presses are conducted by a conveyor 38 to a comminuting device 40, i.e., a grinder or hammer mill, for the purpose of producing a soybean meal with a typical particle size range of 1,000 to 1,200 microns.

Subsequently, the ground soybean meal is conducted by a conveyor 42, to a blending vessel 44 or a battery of blending vessels (44A, 44B, and possibly others) for the purpose of blending in the hydrochloric acid components and further components.

Blending is performed in a batch mode. Weighed quantities of ground soybean meal, hydrochloric acid and other components are entered into the blending vessel wherein an agitating arm stirs the solids and liquid for a time period selected to insure homogeneity of the product and complete absorption of the hydrochloric acid component into the soybean component. The completeness of the blending is typically achieved by agitating for a period of 15 to 30 minutes.

A range of formulations useful for preventing or treating parturient hypocalcemia or milk fever is within the scope of the present invention. A key ingredient of each formulation is a mix of hydrochloric acid in the strength of up to 22 Baumé and the specially treated soybean meal with its high bypass and high palatability factors as discussed above.

An often desirable addition ingredient is one to promote easy flow of the feed mix through feed bins, spouts, conveyors and the like. An example of such an ingredient is feed grade talc (hydrous magnesium silicate). A range of 10 to 30 parts by weight of vermiculite to 1000 parts by weight of the feed formulation is added to insure easy flowability.

An important mineral of any dairy cattle diet is Mg, as lack of it in the diet could cause, as a minimum loss of appetite and reduced dry matter digestibility and, at worst, could cause grass tetany, a condition which can cause anorexia, hyperirritability, convulsions or even death (Dairy Cattle Science, M. E. Ensminger, 3d Ed. (1993) pp. 214–215). This mineral is best supplied in the form of magnesium oxide. One to two parts by weight of magnesium oxide should be added to each one hundred parts of the feed formulation.

In many cases, any formulation of this invention may be fed in conjunction with other feed rations containing protein. In such cases, it is appropriate to reduce the protein level in the formulation by mixing in lower protein containing ingredients, such as beet pulp, dried brewers grains, or distiller dried grains. For example, starting with a mixture of one part by weight of the specially prepared soybean meals and two parts by weight of hydrochloric acid of 22 Baumé and adding two to three parts by weight of beet pulp and three to five parts of dried brewers grains or distillers dried grains and one third of a part by weight of feed grade lime stone, produces a product with a protein content in the 15 to 20% by weight range, and which exhibits the curing or preventing characteristics of the present invention.

A further advantage of adding beet pulp, dried brewers grains or distillers dried grains is that these components are low in moisture (typically 6% by weight) and thus can absorb some of the moisture added with the hydrochloric acid component, thus improving flowability of the end product.

Still another advantage of adding beet pulp, dried brewers grains or distillers dried grains is that these components are low in potassium (typically 0.6% by weight), while the specially treated soybean meal is typically somewhat high in potassium (1.2% by weight). As Ensminger states (Dairy Cattle Science, M. E. Ensminger, 3d Ed. (1993) pp. 214–215), "Excessive levels of potassium have been found to interfere with magnesium absorption. Also, excessive levels of potassium, along with high levels of phosphorus, increase the incidence of phosphatic urinary calculi." By adding the beet pulp, dried brewers grains or distiller dried grains in the ratios indicated, potassium levels can typically be reduced to 0.65 to 0.70% by weight of the total protein components, i.e., the total of the specially produced soybean meal and beet pulp and dried brewers grains or distiller dried grains.

EXAMPLE I

An existing facility for comminuting, heating and mechanically extracting soybeans in accordance with the techniques of this invention provided the soybean meal component for a blending plant for product to inhibit the effects of or reduce the risk of contracting milk fever.

Raw soybeans were fed to the plant at roughly 800 tons per day. The comminuted soybeans were fed to an indirectly steam-heated rotary dryer which was operated in a manner to produce soybean particles which were heated over a period of roughly 20 minutes (plus or minus 2 minutes) to a temperature of 290 degrees Fahrenheit (plus or minus 5 degrees Fahrenheit). The soybean particles were discharged from the kiln at roughly 2 to 3% final moisture by weight.

The heated soybeans from the kiln were conducted to a bank of eighteen Dupps 10 Pressor screw presses with specially modified shafts operating in parallel. Each press produced roughly 6 tons of crude soybean oil per day and 35 tons of cake. Cake discharge temperatures are typically about 280 to 321° F.

The pieces of cake discharge were conducted to grinder to produce a meal with a particle size range of 1,000 to 1,200 microns. Subsequently, the ground meal was conducted to a cooler to reduce temperature to a safe storage temperature of 120° F. or below.

Meal from storage was introduced into a 10 ft. long, 4 ft. wide and 5 ft. deep ribbon blender in which approximately 3,200 lbs of soybean meal was ribbon blended with 800 lbs of 22 Baume hydrochloric add solution. Blending proceeded for a period of 30 minutes. The resulting mixture is available under the commercial trademark SoyChlor® 37. Its blended crude protein content is 37%.

EXAMPLE II

In another example, 160 lbs. of feed grade calcium carbonate was added in the blending step to reduce the volatility of the hydrochloric acid component, thereby reducing the hydrochloric acid odor.

EXAMPLE III

In still another example, 410 lbs of soybean meal as prepared above was blended with 820 lbs of hydrochloric acid of 22 Baume,, 980 lbs of beet pulp, 1,640 lbs of dried brewers grains or distillers dried grains, and 160 lbs of feed grade lime stone to produce 4,010 lbs of product following 30 minutes of blending. This product is commercially available as SoyChlor® 16. Its blended crude protein content is 16% by weight.

EXAMPLE IV

In a further example, 40 to 80 lbs. of magnesium oxide were added to the above formulation to increase magnesium ion concentration to a desirable level.

EXAMPLE V

In still a further example, 20 lbs. of microlite or feed grade vermiculite were added to the mix described above to improve the flow properties of the mixture.

We claim:

1. A formulation for reducing the risk of or inhibiting the effects of parturient hypocalcemia or milk fever, comprising:

one part by weight of 18 to 22 Baumé hydrochloric acid and up to four parts by weight high bypass soybean meal obtained from soybeans prepared according to the steps of:

a) comminuting the soybeans to crack open their hulls and shatter their kernels;

b) heating the comminuted soybeans in a high-temperature reactor to elevated temperatures in the range of 235 to 350 degrees Fahrenheit;

c) maintaining the soybeans at elevated temperatures for a period of 1 to 60 minutes;

d) partially removing the oil contained in the soybeans by mechanical means; and e) grinding the soybean cake produced by mechanical means to produce a soybean meal with a particle size range of 1000 to 1200 microns;

feed components other than soybean meal which further enhance feed value and palatability of the formulation; and minerals that are either essential to the animal's well being and/or positively affect the negative dietary cation-anion difference which governs calcium metabolism.

2. The formulation according to claim 1 wherein one-fifth part of feed grade calcium carbonate to each part of hydrochloric acid is added to reduce volatility of the hydrochloric acid for the purpose of reducing hydrochloric acid odor.

3. The formulation according to claim 2 wherein to each one-half part of the soybean meal is added 1 to 1.5 parts by weight of beet pulp, 1.5 to 2.5 parts by weight of dried brewers grains or distillers dried grains and 1 part by weight of hydrochloric acid of 18–22 Baumé.

4. The formulation according to claim 3 further including one-half to 1 part by weight of magnesium oxide for each fifty parts by weight of the formulation.

5. The formulation according to claim 4 further including 5 to 15 parts by weight feed grade hydrous magnesium silicate for each 500 parts by weight of the formulation.

6. A method for preparing a feed formulation with properties to reduce the risk of or inhibiting the effects of parturient hypocalcemia comprising the following steps:

preparing a high bypass protein soybean meal according to the steps of:

a) comminuting the raw soybeans to crack open their hulls and shatter their kernels;

b) heating the comminuted soybeans in a high-temperature reactor to elevated temperatures in the range of 235 to 350 degrees Fahrenheit;

c) maintaining the soybeans at the elevated temperatures for a period of 1 to 60 minutes;

d) partially removing the oil contained in the soybeans by mechanical means;

e) grinding the soybean cake produced by mechanical means to produce a high bypass protein soybean meal with a particle size range from 1000 to 1200 microns;

blending into the high bypass protein meal up to 25 percent by weight of up to 22 Baumé hydrochloric acid solution; and blending into the formulation one part by weight of feed grade limestone for each five parts by weight of hydrochloric acid.

7. The method according to claim 6 further including the blending of the following components into the formulation:

beet pulp;

either dried brewers grains or distillers dried grains;

magnesium oxide; and feed grade hydrous magnesium silicate.

8. A feed for treating milk fever, comprising:

a homogenous blend including three parts by weight high bypass protein meal prepared from soybeans according to the steps of:

a) comminuting the raw soybeans to crack open their hulls and shatter their kernels;

b) heating the comminuted soybeans in a high-temperature reactor to elevated temperatures in the range of 235 to 350 degrees Fahrenheit;

c) maintaining the soybeans at the elevated temperatures for a period of 1 to 60 minutes;

d) partially removing the oil contained in the soybeans by mechanical means;

e) grinding the soybean cake produced by mechanical means to produce a high bypass protein soybean meal with a particle size range from 1000 to 1200 microns; and one part by weight 18–22 Baumé hydrochloric acid, wherein the hydrochloric acid is completely absorbed by the high bypass protein meal.

9. A method for preparing a feed formulation with properties to reduce the risk of or inhibiting the effects of parturient hypocalcemia comprising the following steps:

preparing a high bypass protein soybean meal according to the steps of:

a) comminuting the raw soybeans to crack open their hulls and shatter their kernels;

b) heating the comminuted soybeans in a high-temperature reactor to elevated temperatures in the range of 235 to 350 degrees Fahrenheit;

c) maintaining the soybeans at the elevated temperatures for a period of 1 to 60 minutes;

d) partially removing the oil contained in the soybeans by mechanical means;

e) grinding the soybean cake produced by mechanical means to produce a high bypass protein soybean meal with a particle size range from 1000 to 1200 microns; and blending into the high bypass protein meal up to 25 percent by weight of up to 22 Baumé hydrochloric acid solution.

\* \* \* \* \*